United States Patent [19]

Chokai et al.

[11] Patent Number: 5,342,845
[45] Date of Patent: Aug. 30, 1994

[54] INDOLE DERIVATIVES AND DRUGS

[75] Inventors: Shoichi Chokai, Kyoto; Tomiyoshi Aoki; Yojiro Ukai, both of Shiga, all of Japan

[73] Assignee: Nippon Shinyaku Company Limited, Japan

[21] Appl. No.: 983,513

[22] PCT Filed: Aug. 29, 1991

[86] PCT No.: PCT/JP91/01148
§ 371 Date: Feb. 26, 1993
§ 102(e) Date: Feb. 26, 1993

[87] PCT Pub. No.: WO92/04347
PCT Pub. Date: Mar. 19, 1992

[30] Foreign Application Priority Data

Aug. 31, 1990 [JP] Japan .................. 2-231030
Oct. 2, 1990 [JP] Japan .................. 2-265847

[51] Int. Cl.$^5$ .................. A61K 31/435; C07D 453/02
[52] U.S. Cl. .................. 514/305; 546/133
[58] Field of Search .................. 514/305; 546/133

[56] References Cited

U.S. PATENT DOCUMENTS 5,175,173 12/1992 Sun .................. 546/133

FOREIGN PATENT DOCUMENTS 261964 3/1988 European Pat. Off. .
491664 6/1992 European Pat. Off. .
512350 11/1992 European Pat. Off. .
WO90/14347 11/1990 PCT Int'l Appl. .

*Primary Examiner*—Johann Richter
*Assistant Examiner*—Catherine S. K. Scalzo
*Attorney, Agent, or Firm*—Rosenman & Colin

[57] ABSTRACT

The object of the invention is to provide a novel compound having serotonin antagonist activity.

The invention is directed to an indolecarboxamide derivative of the following general formula [I] and a serotonin antagonist composition comprising the same derivative as an active ingredient.

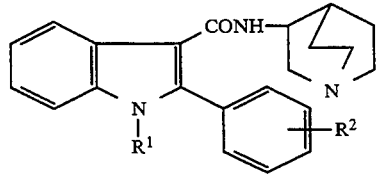

(wherein $R^1$ is a lower alkyl and $R^2$ is hydrogen, a halogen, a lower alkyl or a lower alkoxy.)

The compound of the invention is effective as a gastrointestinal motor activity regulator, antimigraine, antipsychotic or antianxiety drug. The compound is also effective as a therapeutic drug for dementia or orthostatic hypotension.

35 Claims, No Drawings

INDOLE DERIVATIVES AND DRUGS

This application is based on International Application PCT/JP91/01148, filed Aug. 29, 1991 which in turn corresponds to:

Hei-2/231,030 filed with the JPO Aug. 31, 1990, and Hei-2/265,847 filed with the JPO Oct. 2, 1990.

TECHNICAL FIELD

The present invention relates to an indolecarboxamide derivative of the following general formula [I]

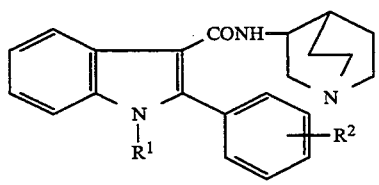

(wherein $R^1$ is a lower alkyl; $R^2$ is hydrogen, a halogen, a lower alkyl or a lower alkoxy ) and a pharmaceutically acceptable salt thereof. The compound of the invention has a serotonin antagonistic activity and is of use as an antiemetic, a gastrointestinal motor activity regulator, an antimigraine, an antipsychotic, an antianxietic and the like.

Furthermore, the compound of the invention has an ameliorative effect on deficits of learning and memory improving activity and is therefore of use in the treatment of vascular dementia and Alzheimer's disease. In addition, the compound of the invention is useful as a therapeutic and prophylactic agent for orthostatic hypotension and syncope as well.

BACKGROUND ART

Serotonin (5-HT) is a neurotransmitter distributed widely in the animal and vegetable kingdoms and has a broad spectrum of physiological actions. It is generally considered that there are three subtypes of serotonin receptors, viz. 5-$HT_1$, 5-$HT_2$ and 5-$HT_3$.

Regarding the functions of 5-$HT_3$ receptors, promotion of release of transmitters (noradrenalin, acetylcholine) from the nerves, depoloralization of the sympathetic and parasympathetic ganglions, reflex bradycardia and dolorogenesis are known. However, much remains to be elucidated about the functions of 5-$HT_3$ receptors and the mechanisms of the antiemetic and psychotropic effects of its antagonists have not been established as yet. GR-38032F (ondansetron), a selective antagonist of 5-$HT_3$ receptors, is said to markedly inhibit the emesis associated with the administration of anticancer drugs and, moreover, exhibit excellent anxiolytic and antipsychotic actions.

As indole derivatives having an azabicyclic group, a variety of compounds have heretofore been reported (e.g. Japanese Kokai Tokkyo Koho 63-277622, 63-277623, 62-116580 and 61-212521 and Japanese Patent Application 1-130899).

However, indole-3-carboxamide derivatives having a phenyl group in the 2-position of the indole nucleus have never been described in literatures so far nor are they included in the claims of any of the above-cited patent and pending patent literature.

DISCLOSURE OF INVENTION

The inventors of the present invention did much explorations to obtain a compound surpassing any of the hitherto-known serotonin antagonists in efficacy, safety and duration of action. It is, therefore, an object of the invention to provide a novel compound having serotonin antagonistic activity.

The gist of the present invention resides in the very structure of compounds of general formula [I]. The compound of the invention is not only a novel compound but has excellent pharmacological actions and a low toxicity feature as will be described hereinafter.

Referring to general formula [I], the lower alkyl $R^1$ is preferably a straight or branched alkyl group of 1 to 4 carbon atoms such as methyl, ethyl, n-propyl, isopropyl, n-butyl, isobutyl or sec-butyl. The halogen as represented by $R^2$ may be chlorine, fluorine, bromine or iodine and the lower alkyl is preferably a straight or branched alkyl group of 1 to 4 carbon atoms such as methyl, ethyl, n-propyl, isopropyl, n-butyl, isobutyl or sec-butyl. And the lower alkoxy represented by $R^2$ is preferably a straight or branched alkoxy group of 1 to 4 carbon atoms such as methoxy, ethoxy, n-propoxy, isopropoxy, n-butoxy, isobutoxy or sec-butoxy.

The compound of the present invention can be produced, for example, by the following and other processes.

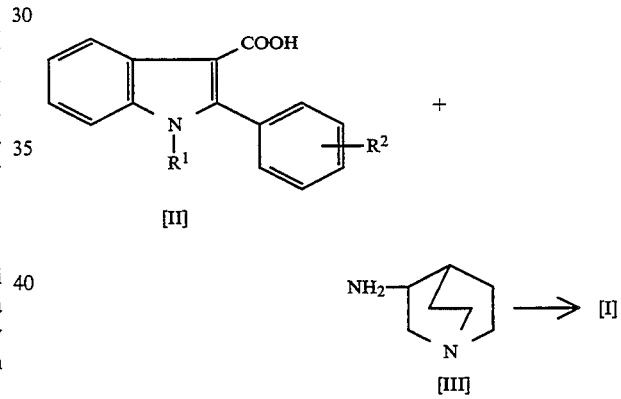

wherein $R^1$ and $R^2$ have the same meanings as defined hereinbefore.

An indole-3-carboxylic acid [II] or its reactive derivatives is reacted with quinuclidylamine [III] to synthesize [I].

This amidation reaction can be conducted in the per se known manner.

For example, there may be reckoned a process using a reactive derivative of [II], e.g. an acid halide (e.g. acid chloride, acid bromide, etc.), a lower alkyl ester or an active ester (e.g. p-nitrophenyl ester, p-nitrobenzyl ester, p-chlorophenyl ester, 1-hydroxybenzotriazole ester, etc.), an imidazolide or a mixed acid anhydride (e.g. a mixed anhydride with a lower alkyl carbonate, or a mixed acid anhydride with a lower alkyl phosphate), for instance, in an appropriate manner or a process comprising condensing [II] with [III] directly with the aid of a condensing agent.

Referring to the use of an acid halide, the halide of [II] is reacted with [III] in the presence of a base in a solvent inert to the reaction at −20° C. to 30° C. The solvent which can be used includes, among others, ethers such as ether, tetrahydrofuran and dioxane, halogenated hydrocarbons such as methylene chloride and chloroform, hydrocarbons such as benzene, toluene and xylene, N,N-dimethylformamide, pyridine, water or a mixture of such solvents.

As base, inorganic bases such as potassium carbonate, sodium hydroxide and potassium hydroxide and tertiary organic bases such as pyridine, triethylamine, tributylamine and dimethylaniline may be used.

The suitable reaction time, which may vary with different species of starting materials, base and solvent used, is generally 30 minutes to 12 hours.

The amount of the acid halide to be used is preferably 1 to 1.2 moles per mole of [III] in ordinary cases.

For the direct condensation in the presence of a condensing agent, [II] is reacted with [III] in the presence of a condensing agent generally in a solvent inert to the reaction at −20° to 80° C. The solvent may be the same as that mentioned above.

Illustrative condensing agents are carbodiimides such as dicyclohexylcarbodiimide, quaternary pyridinium salts such as 2-chloro-N-methylpyridinium iodide and 2-methanesulfonyloxy-N-methylpyridinium iodide, diphenylphosphorylazide and so on.

The starting compound [II] can be synthesized in accordance with the following reaction schema, although details are set forth in the reference examples.

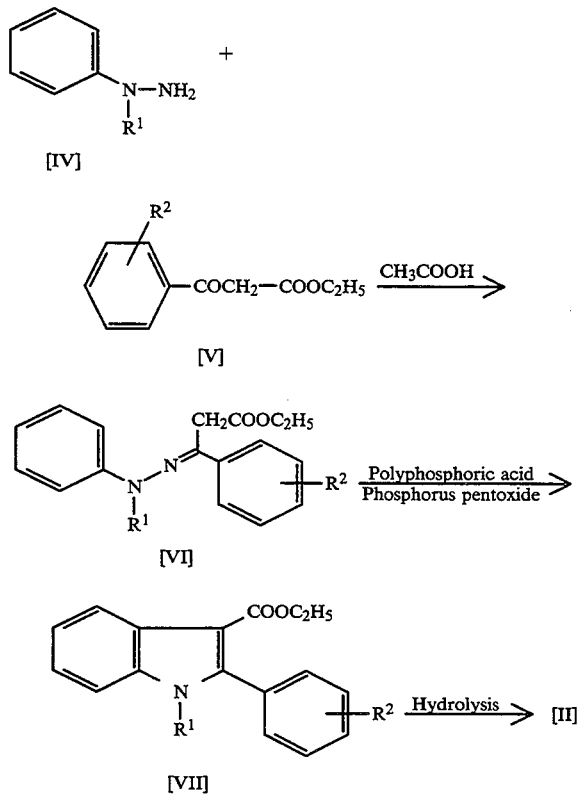

(wherein $R^1$ and $R^2$ have the same meanings as defined hereinbefore)

Thus, an 1-alkyl-1-phenylhydrazine [IV] is condensed with a benzoyl acetate derivative [V] in acetic acid to give an ethyl 3-phenyl-3-(N-alkyl-N-phenylhydrazono)propionate derivative [VI] which is then subjected to cyclization reaction with a mixture of polyphosphoric acid and phosphorus pentoxide to give an ethyl 2-phenyl-1-alkylindolecarboxylate derivative [VIII] which is finally hydrolyzed to [II].

It is clear that the compound of the present invention has an asymmetric carbon. Therefore, there are optical isomers, viz. R- and S-forms, and these respective optical isomers and the racemic mixture thereof are also included in the scope of the present invention.

The optical isomers can be obtained from the racemic mixture, obtained as above, by optical resolution utilizing its basicity, that is to say by using an optically active acid (tartaric acid, dibenzoyltartaric acid, mandelic acid, 10-camphorsulfonic acid, etc.) in the per se known manner or alternatively by using an optically active starting compound [III] prepared beforehand.

The desired compound [I] thus prepared can be isolated and purified as the free base or in the form of an acid addition salt by the per se known procedures such as concentration, pH adjustment, redistribution, solvent extraction, crystallization, fractional distillation, chromatography and so on.

Illustrative acid addition salt mentioned above are salts with mineral acids such as hydrochloric acid, hydrobromic acid, sulfuric acid, nitric acid and phosphoric acid and salts with organic acids such as acetic acid, citric acid, tartaric acid, maleic acid, succinic acid, fumaric acid, p-toluenesulfonic acid, benzenesulfonic acid and methanesulfonic acid.

When of the compound of the present invention is administered as a drug to man or other animals, it can be administered as it is or as formulated beforehand into a pharmaceutical composition containing 0.1 to 99.5%, preferably 0.5 to 90%, of the compound in a pharmaceutically acceptable, nontoxic and inert excipient.

The excipient mentioned above may be one or more solid, semisolid or liquid diluents, fillers and/or other formulation auxiliaries. Such a pharmaceutical composition is preferably administered in unit dosage forms. The pharmaceutical composition of the invention can be administered intravenously, orally, into tissues, topically (transdermally etc.) or rectally. Of course, dosage forms suitable for the respective routes of administration should be employed. Particularly preferred are oral or intravenous administration.

The dosage as an antiemetic drug should preferably be adjusted according to the patient's age, body weight and other factors, the route of administration and the nature and severity of the disease. The generally recommended dosage for oral administration to an adult human is 0.1 to 100 mg/body/day or preferably 0.1 to 10 mg/body/day and that for intravenous administration is 0.001 to 10 mg/body/day or preferably 0.01 to 1 mg/body/day.

The required dosage may be somewhat less or more, depending on individual cases. The administration may also be subdivided so that administration takes place 2 to 4 times per day.

For oral administration, either solid or liquid unit dosage forms such as neat powders, powders, tablets, dragees, capsules, granules, suspensions, solutions, syrups, drops, sublingual and tablets can be provided.

Neat powders are manufactured by comminuting the active substance to a fine size. Powders are manufactured by comminuting the active substance to a fine size and admixing the resulting neat powder with a pharmaceutical excipient such as an edible carbohydrate, e.g. starch, mannitol, etc., which has been similarly comminuted beforehand. If necessary, a flavoring, preservative, dispersant, colorant, perfume, etc. can also be mixed.

Capsules can be manufactured by preparing neat or formulated powders in the above manner or granules in the manner described hereinafter for tablets and, then, filling gelatin or other capsule shells with the powders or granules. Prior to the filling operation, a lubricant or fluidizing agent, such as colloidal silica, talc, magnesium stearate, calcium stearate or solid polyethylene glycol can be added, each to the powder mixture, to said granules. An improvement in effect of the drug administered may be obtained by adding a disintegrator or solubilizer such as carboxymethylcellulose, carboxymethylcellulose calcium, low-substituted hydroxypropylcellulose, crosscarmelose sodium, carboxymethylstarch sodium, calcium carbonate or sodium carbonate.

Soft capsules can be obtained by suspending and dispersing a finely divided powder of the drug in a mixture of vegetable oil, polyethylene glycol, glycerin and surfactant and wrapping the suspension in a flexible gelatin shell. Tablets can be manufactured by preparing a powdery mixture with use of an excipient, processing it into granules or slags, and after addition of a disintegrator or lubricant, compression-molding the mixture. The powdery mixture can be prepared by mixing the pulverized drug with said diluent or base, with or without addition of a binder (e.g. carboxymethylcellulose sodium, methylcellulose, hydroxypropylcellulose, gelatin, polyvinylpyrrolidone, polyvinyl alcohol, etc.), a dissolution retardant (e.g. paraffin etc.), a reabsorption agent (e.g. a quaternary salt) or an adsorbent (e.g. bentonite, kaolin, dicalcium phosphate, etc.). The powdery mixture can be granulated by wetting it with a binder, such as a syrup, starch paste, gum arabic, a cellulosic or polymeric solution, followed by stirring to mix, drying and granulating. Instead of such a granulation process, the mixture may first be tableted and the resulting slags of imperfect form are comminuted into granules.

To the granules which are manufactured in the above manner, an appropriate lubricant such as stearic acid, stearates, talc or mineral oil can be added for preventing the interadhesion of individual granules. The thus-lubricated mixture is then compression-molded.

Instead of being processed through said granulation and slagging steps, the drug may be admixed with a free-flowing inert carrier followed by directly compression-molding. It is also possible to utilize a transparent or translucent protective coating consisting of a hermetically sealing shellac film, a sugar or polymeric coating or a polished wax coating.

Other oral dosage forms such as solutions, syrups and elixers can also be provided in unit dosage forms so that a given quantity contains a predetermined amount of the compound. Syrups can be manufactured by dissolving a compound in an appropriate flavored aqueous medium, while elixers can be manufactured using a nontoxic alcoholic vehicle. Suspensions can be formulated by dispersing the compound in a nontoxic vehicle. Solubilizers and emulsifiers (e.g. ethoxylated isostearyl alcohol, polyoxyethylene sorbitol ester), preservatives, flavorants (e.g. peppermint oil, saccharin) and other agents can also be added, where necessary.

If necessary, such a unit dosage form for oral administration can be microencapsulated. Said dosage unit may also be coated or embedded in a polymer, wax or the like for prolonged action or sustained release.

For administration into tissues, liquid unit dosage forms for subcutaneous, intramuscular or intravenous administration such as solutions and suspensions, can be utilized. Thus, these preparations can be manufactured by suspending or dissolving a predetermined amount of the active compound in an injectable nontoxic liquid vehicle such as an aqueous or oily medium, and sterilizing the resulting suspension or solution. For isotonization, a nontoxic salt or a solution of the salt may be added to an injectable composition. Moreover, stabilizers, preservatives, emulsifiers and the like may also be employed.

For rectal administration, suppositories can be provided by dissolving or suspending the active compound in a water-soluble or -insoluble solid base, such as polyethylene glycol, cacao butter, semisynthetic oleagenous fat (e.g. Witepsol(TM) or a higher ester (e.g. myristyl palmitate), or a mixture thereof.

BEST MODE FOR CARRYING OUT THE INVENTION

The following reference examples, working examples, test examples and formulation examples of the compound of the present invention are intended to describe the invention in further detail.

REFERENCE EXAMPLE 1

Synthesis of 2-(4-methoxyphenyl)1-methylindole-3-carboxylic acid (1) Synthesis of ethyl p-methoxybenzoylacetate In 60 ml of tetrahydrofuran was suspended 18.7 g of 60% sodium hydride followed by addition of 39.4 of diethyl carbonate. Then, a solution of 25 g of p-methoxyacetophenone in 70 ml of THF was added dropwise with refluxing and the mixture was further refluxed for 5 hours. After cooling, the reaction mixture was poured slowly into iced water, neutralized with concentrated hydrochloric acid and extracted with ethyl acetate. The extract was washed with water, dried over anhydrous magnesium sulfate and concentrated. The resulting oil was distilled under reduced pressure to provide 30.1 g of the desired compound as a pale yellow oil. b.p. 161°–164° C. (3 mmHg).

(2) Synthesis of ethyl 3-(4-methoxyphenyl)-3-(N-methyl-N-phenylhydrazono)propionate In 60 ml of acetic acid were dissolved 15 g of ethyl p-methoxybenzoylacetate and 8.25 g of 1-methyl-1-phenylhydrazine and the resulting solution was stirred at room temperature for 12 hours. The reaction mixture was poured into iced water and extracted with ethyl acetate. The extract was washed with aqueous solution of sodium hydrogen carbonate and water in that order, dried over anhydrous magnesium sulfate and concentrated to provide 21.8 g of the desired compound as a yellow oil.

(3) Synthesis of 2-(4-methoxyphenyl)-1-methylindole-3-carboxylic acid

To 80 g of 105% polyphosphoric acid was added 27 g of phosphorus pentoxide and the mixture was stirred, whereupon heat was evolved to give a substantially homogeneous solution. 9.25 g of ethyl 3-(4-methoxyphenyl)-3-(N-methyl-N-phenylhydrazone)propionate was added thereto and the mixture was stirred at room temperature for 2 hours. The reaction mixture was poured into iced water and extracted with ethyl acetate. The extract was washed with water, dried over anhydrous magnesium sulfate and concentrated. To the residue was added isopropyl ether and the resulting crystals were recovered by filtration to give 3.7 g of pale yellow crystals. To the crystals were added 60 ml of methanol and 20 ml of 10% aqueous solution of sodium hydroxide and the mixture was refluxed for 40 hours. The reaction mixture was then concentrated and water was added to the residue to dissolve and washed with ethyl acetate, followed by addition of concentrated hydrochloric acid. The resulting crystals were recovered by filtration to give 2.8 g of the desired compound as white crystals. m.p. 229°–230.5° C.

The following compounds were obtained in the same manner as above.

2-(2-Methoxyphenyl)-1-methylindole-3-carboxylic acid m.p. 205°–206° C.

2-(2-Ethoxyphenyl)-1-methylindole-3-carboxylic acid m.p. 203°–207° C.

2-(2-Chlorophenyl)-1-methylindole-3-carboxylic acid m.p. 200°–202° C.

2-(3-Chlorophenyl)-1-methylindole-3-carboxylic acid m.p. 215.5°–217° C.

2-(4-Chlorophenyl)-1-methylindole-3-carboxylic acid m.p. 218°–220° C.

2-(2-Fluorophenyl)-1-methylindole-3-carboxylic acid m.p. 189°–190° C.

2-(4-Fluorophenyl)-1-methylindole-3-carboxylic acid m.p. 225°–226° C.

2-(4-Isopropylphenyl)-1-methylindole-3-carboxylic acid

2-Phenyl-1-methylindole-3-carboxylic acid

Reference Example 2

Synthesis of (S)-(−)-3-aminoquinuclidine (1) Synthesis of N-(3-quinuclidinyl)-3-chlorobenzamide In 400 ml of acetonitrile was suspended 25 g of m-chlorobenzoic acid and while the suspension was stirred with ice-cooling, 39.5 g of N,N′-dicyclohexylcarbodiimide and 27.0 g of 1-hydroxybenzotriazole monohydrate were added. The mixture was stirred for 2 hours. Then, 20.2 g of 3-aminoquinuclidine was added and the mixture was further stirred with ice-cooling for 2 hours and, then, at room temperature for 20 hours. The reaction mixture was filtered to remove insolubles and the solvent was evaporated off. The residue was dissolved by addition of diluted hydrochloric acid and washed twice with ethyl acetate. The aqueous layer was neutralized with aqueous solution of sodium hydroxide and extracted with chloroform. The extract was washed with water and dried over anhydrous magnesium sulfate and the chloroform was evaporated off to give 42.1 g of the desired compound as white crystals.

(2) Synthesis of (S)-(−)-N-(3-quinuclidinyl)-3-chlorobenzamide hydrochloride

In 60 ml of methanol was dissolved 23 g of N-(3-quinuclidinyl)-3-chlorobenzamide followed by addition of a solution of D-(−)-tartaric acid (13 g) in 40 ml of methanol. The mixture was ice-cooled and the resulting crystals were recovered by filtration. To the crystals was added 350 ml of methanol and the mixture was refluxed for a while. After cooling, the crystals were collected by filtration. The above operation was repeated twice and the crystals obtained were dissolved in water and sodium hydroxide solution was added. This mixture was extracted with chloroform and the extract was washed with water and dried over anhydrous magnesium sulfate. The solvent was then evaporated off to obtain a colorless oil. This oil was treated with ethanolic hydrochloric acid in acetone and the precipitated hydrochloride was recovered by filtration to give 11.4 g of the desired compound as white crystals. m.p. 244°–246° C.

$[\alpha]^{20}_D = -16.5°$ (C=1, CH$_3$OH)

(3) Synthesis of (S)-(−)-3-aminoquinuclidine

To 11.2 g of (S)-(−)-N-(3-aminoquinuclidinyl)-3-chlorobenzamide hydrochloride was added 40 ml of concentrated hydrochloric acid and the mixture was refluxed for 6 hours. The reaction mixture was cooled and filtered to remove insolubles and the filtrate was concentrated and dried. To the residue was added ethanol and the resulting crystals were recovered by filtration to provide 6.9 g of (S)-(−)-3-aminoquinuclidine dihydrochloride. m.p. not lower than 260° C.

$[\alpha]^{20}_D = -24.5°$ (C=1, H$_2$O)

The crystals obtained above were dissolved in water, and an aqueous solution of sodium hydroxide was added and extracted with chloroform. The extract was dried over anhydrous magnesium sulfate and concentrated to give 3.2 g of the desired compound as white crystals. m.p. 118°–121° C.

EXAMPLE 1

N-(1-Azabicyclo[2,2,2]octo-3-yl)-1-methyl-2-phenylindo-le-3-carboxamide hydrochloride In 8 ml of N,N-dimethylformamide (DMF) was dissolved 1.0 g of 2-phenyl-1-methylindole-3-carboxylic acid and under ice-cooling and stirring, 0.90 g of N,N′-dicyclohexylcarbodiimide and 0.67 g of 1-hydroxybenzotriazole monohydrate were added thereto.

After 2 hours of stirring, 0.50 g of 3-aminoquinuclidine was added and the mixture was further stirred with ice-cooling for 2 hours and at room temperature for 15 hours. The reaction mixture was then filtered to remove insolubles and the solvent was evaporated off. The residue was dissolved by addition of diluted hydrochloric acid. The aqueous layer was washed with ethyl acetate, neutralized with aqueous solution of sodium hydroxide and extracted with chloroform. The extract was washed with water and dried over anhydrous magnesium sulfate and the chloroform was evaporated off under reduced pressure. The resulting pale yellow oil was dissolved in acetone and converted to the hydrochloride by addition of 10% HCl in ethanol. Ether was added thereto to crystallize. The crystals were recovered by filtration and recrystallized from the mixed solution of ethanol and ether to give 1.6 g of the desired compound as white crystals. m.p. 269°–271° C.

Elemental analysis (for C$_{23}$H$_{25}$N$_3$O.HCl) Calcd. (%): C, 69.77; H, 6.62; N, 10.61 Found (%): C, 69.40; H, 6.91; N, 10.61

EXAMPLE 2

(S)-(−)-N-(1-Azabicyclo[2,2,2]octo-3-yl)-2-(4-methoxyphenyl)-1-methylindole-3-carboxamide hydrochloride In 14 ml of DMF was suspended 1.5 g of 2-(4-methoxyphenyl)-1-methylindole-3-carboxylic acid and under ice-cooling and stirring, 1.21 g of N,N′-dicyclohexylcarbodiimide and 0.90 g of 1-hydroxybenzotriazole monohydrate were added thereto.

After 2 hours of stirring, 0.68 g of (S)-(−)-3-aminoquinuclidine was added thereto and the mixture was stirred with ice-cooling for 2 hours and, then, at room temperature for 20 hours. The reaction mixture was filtered to remove insolubles, the solvent was then evaporated off, and the residue was dissolved by addition of diluted hydrochloric acid. The solution was washed with ethyl acetate and the aqueous layer was neutralized with aqueous solution of sodium hydroxide and extracted with chloroform. The extract was washed with water and dried over anhydrous magnesium sulfate and the chloroform was then evaporated off under reduced pressure. The resulting pale yellow crystals were dissolved in acetone, followed by addition of 10% HCl in ethanol to give the hydrochloride. Ether was added thereto to crystallize. The crystals were recovered by filtration and recrystallized from the mixed solvent of chloroform and ether to give 1.5 g of the desired compound as white crystals. m.p. 155°–158° C.

Elemental analysis (for $C_{24}H_{27}N_3O \cdot HCl$) Calcd. (%): C, 67.67; H, 6.63; N, 9.86 Found (%): C, 67.35; H, 6.78; N, 9.53 $[\alpha]^{20}_D = -13.2°$ (C=1, $H_2O$)

In the same manner as Examples 1 and 2, the following compounds were obtained.

EXAMPLE 3

(S)-(−)-N(1-Azabicyclo[2,2,2]octo-3-yl)-2-phenyl-1-methylindole-3-carboxamide hydrochloride m.p. 259.5°–261° C.

Elemental analysis (for $C_{23}H_{25}N_3O \cdot HCl$) Calcd. (%): C, 69.77; H, 6.62; N, 10.61 Found (%): C, 69.40; H, 6.73; N, 10.42 $[\alpha]^{20}_D = -15.57°$ (C=1, $H_2O$)

EXAMPLE 4

N-(1-Azabicyclo[2,2,2]octo-3-yl)-2-(4-methoxyphenyl)-1-methylindole-3-carboxamide hydrochloride m.p. 250°–252° C. Elemental analysis (for $C_{24}H_{27}N_3O_2 \cdot HCl$) Calcd. (%): C, 67.67; H, 6.63; N, 9.86 Found (%): C, 67.40; H, 6.73; N, 9.70

EXAMPLE 5

N-(1-Azabicyclo[2,2,2]octo-3-yl)-2-(4-isopropylphenyl)-1-methylindole-3-carboxamide hydrochloride m.p. 214°–216° C. Elemental analysis (for $C_{26}H_{31}N_3O \cdot HCl$) Calcd. (%): C, 71.30; H, 7.36; N, 9.59 Found (%): C, 71.01; H, 7.50; N, 9.40

EXAMPLE 6

N-(1-Azabicyclo[2,2,2]octo-3-yl)-2-(4-chlorophenyl)-1-methylindole-3-carboxamide hydrochloride m.p. 240°–243° C. Elemental analysis (for $C_{23}H_{24}ClN_3O \cdot HCl$) Calcd. (%): C, 64.19; H, 5.86; N, 9.76 Found (%): C, 63.92; H, 5.64; N, 9.83

EXAMPLE 7

(S)-(−)-N-(1-Azabicyclo[2,2,2]octo-3-yl)-2-(4-chlorophenyl)-1-methylindole-3-carboxamide hydrochloride Elemental analysis (for $C_{23}H_{24}ClN_3O \cdot HCl$) Calcd. (%): C, 64.19; H, 5.86; N, 9.76 Found (%): C, 64.31; H, 5.93; N, 9.52 $[\alpha]^{20}_D = -5.71°$ (C=1, $H_2O$)

EXAMPLE 8

N-(1-Azabicylo[2,2,2]octo-3-yl)-2-(2-methoxyphenyl)-1-methylindole-3-carboxamide hydrochloride m.p. 275° C. Elemental analysis (for $C_{24}H_{27}N_3O_2 \cdot HCl$) Calcd. (%): C, 67.67; H, 6.63; N, 9.86 Found (%): C, 67.37; H, 6.75; N, 9.50

EXAMPLE 9

N-(1-Azabicyclo[2,2,2]octo-3-yl)-2-(4-fluorophenyl)-1-methylindole-3-carboxamide hydrochloride m.p. 275.5°–277° C. Elemental analysis (for $C_{23}H_{24}FN_3O \cdot HCl$) Calcd. (%): C, 66.74; H, 6.09; N, 10.15 Found (%): C, 66.57; H, 6.26; N, 10.16

EXAMPLE 10

N-(1-Azabicyclo[2,2,2]octo-3-yl)-2-(2-chlorophenyl)-1-methylindole-3-carboxamide hydrochloride m.p. 197°–199° C.

Elemental analysis (for $C_{23}H_{24}ClN_3O \cdot HCl$) Calcd. (%): C, 64.19; H, 5.86; N, 9.76 Found (%): C, 64.41; H, 5.63; N, 9.58

EXAMPLE 11

(S)-(−)-N-(1-Azabicyclo[2,2,2]octo-3-yl)-2-(2-methoxyphenyl)-1-methylindole-3carboxamide hydrochloride m.p. 242°–243° C. Elemental analysis (for $C_{24}H_{27}N_3O \cdot HCl$) Calcd. (%): C, 67.67; H, 6.63; N, 9.86 Found (%): C, 67.30; H, 6.38; N, 9.79

$[\alpha]^{20}_D = -17.5°$ (C=1, $H_2O$)

EXAMPLE 12

(S)-(31 )-N-(1-Azabicyclo[2,2,2]octo-3-yl)-2-(2-chlorophenyl)-1-methylindole-3-carboxamide hydrochloride m.p. 194°–196° C. Elemental analysis (for $C_{23}H_{24}ClN_3O \cdot HCl$) Calcd. (%): C, 64.19; H, 5.86; N, 9.76 Found (%): C, 64.38; H, 5.62; N, 9.83 $[\alpha]^{20}_D = -24.5°$ (C=1, $H_2O$)

EXAMPLE 13

(S)-(−)-N-(1-Azabicyclo[2,2,2]octo-3-yl)-2-(2-fluorophenyl)-1-methylindole-3-carboxamide hydrochloride m.p. 215° C. Elemental analysis (for $C_{23}H_{24}FN_3O \cdot HCl$) Calcd. (%): C, 66.74; H, 6.09; N, 10.15 Found (%): C, 66.41; H, 6.40; N, 9.80

$[\alpha]^{20}_D = -24.92°$ (C=1, $H_2O$)

EXAMPLE 14

(S)-(31 )-N-(1-Azabicyclo[2,2,2]octo-3-yl)-2-(-3-chlorophenyl)-1-methylindole-3-carboxamide hydrochloride m.p. 230° C. Elemental analysis (for $C_{23}H_{24}ClN_3O \cdot HCl$) Calcd. (%): C, 64.19; H, 5.86; N, 9.76 Found (%): C, 63.90; H, 6.01; N, 9.50

$[\alpha]^{20}_D = -16.46°$ (C=1, $H_2O$)

EXAMPLE 15

(S)-(31 )-N-(1-Azabicyclo[2,2,2]octo-3-yl)-2-(-2-ethoxyphenyl)-1-methylindole-3-carboxamide hydrochloride m.p. 220° C. Elemental analysis (for $C_{25}H_{229}N_3O_2 \cdot HCl$) Calcd. (%): C, 68.40; H, 6.66; N, 9.57 Found (%): C, 68.01; H, 6.96; N, 9.30

$[\alpha]^{20}_D = -15.39°$ (C=1, $CH_3OH$)

FORMULATION EXAMPLE 1

According to the following formula, 1 ml of an injectable solution was prepared by the established pharmaceutical procedure.

| Formula | |
| --- | --- |
| Compound of Example 8 | 1 mg |
| Sodium chloride | 9 mg |
| Water for injection | q. s. |

FORMULATION EXAMPLE 2

According to the following formula, 1 ml of an injectable solution was prepared by the established pharmaceutical procedure.

| Formula | |
| --- | --- |
| Compound of Example 8 | 1 mg |
| Glucose | 48 mg |
| Sodium dihydrogen phosphate | 1.25 mg |
| Sodium monohydrogen phosphate | 0.18 mg |
| Water for injection | q. s. |

FORMULATION EXAMPLE 3

According to the following formula, 1 ml of an injectable solution was prepared by the established pharmaceutical procedure.

| Formula | |
| --- | --- |
| Compound of Example 10 | 1 mg |
| Glucose | 48 mg |
| Sodium dihydrogen phosphate | 1.25 mg |
| Sodium monohydrogen phosphate | 0.18 mg |
| Water for injection | q. s. |

FORMULATION EXAMPLE 4

According to the following formula, 1 ml of an injectable solution was prepared by the established pharmaceutical procedure.

| Formula | |
| --- | --- |
| Compound of Example 8 | 1 mg |
| Sorbitol | 48 mg |
| Benzyl alcohol | 20 mg |
| Sodium dihydrogen phosphate | 2.5 mg |
| Sodium monohydrogen phosphate | 0.36 mg |
| Water for injection | q. s. |

FORMULATION EXAMPLE 5

According to the following formula, 1 ml of an injectable solution was prepared by the established pharmaceutical procedure.

| Formula | |
| --- | --- |
| Compound of Example 10 | 1 mg |
| Sorbitol | 48 mg |
| Benzyl alcohol | 20 mg |
| Sodium dihydrogen phosphate | 2.5 mg |
| Sodium monohydrogen phosphate | 0.36 mg |
| Water for injection | q. s. |

FORMULATION EXAMPLE 6

According to the following formula, a tablet was prepared by the established pharmaceutical procedure.

| Formula | |
| --- | --- |
| Compound of Example 11 | 3 mg |
| Lactose | 58 mg |
| Corn starch | 30 mg |
| Crystalline cellulose | 20 mg |
| Hydroxypropylcellulose | 7 mg |
| Magnesium stearate | 2 mg |

FORMULATION EXAMPLE 7

According to the following formula, a tablet was prepared by the established pharmaceutical procedure.

| Formula | |
| --- | --- |
| Compound of Example 12 | 3 mg |
| Lactose | 58 mg |
| Corn starch | 30 mg |
| Crystalline cellulose | 20 mg |
| Hydroxypropylcellulose | 7 mg |
| Magnesium stearate | 2 mg |

Results of pharmacological tests indicating the usefulness of representative compounds of the invention are given below.

1. Inhibition of Bezold-Jarisch reflex

The effect of the test compound on the serotonin-induced decrease in heart rate (Bezold-Jarisch reflex) was investigated in male rats, 6–8 weeks of age, with reference to the method of Richardson, et al. (Richardson, B. P., Engel, G., Donatsch, P. and Stadle, P. A.: Identification of serotonin-receptor subtypes and their specific blockade by a new class of drugs; Nature 316, 126–131 (1985)). With the animal immobilized in dorsal position under urethane anesthesia, 0.1 mg/kg of serotonin was administered intravenously before and 5 min after intravenous administration of the test compound and changes in heart rate were recorded. With the % decrease in heart rate as caused by the administration of serotonin preceding administration of the test compound being taken as 100%, the dose of the test compound which inhibited the response by 50% was regarded as $ED_{50}$. The $ED_{50}$ value was calculated by the least square method.

TABLE 1

| Serotonin-induced inhibition of Bezold-Jarisch reflex (rats) | |
| --- | --- |
| Test compound (Example No.) | $ED_{50}$ (µg/kg) |
| 2 | 0.30 |
| 7 | 0.28 |
| 8 | 0.18 |
| 10 | 0.25 |
| 11 | 0.14 |
| 12 | 0.20 |
| ICS-205-930 | 1.79 |

As seen from Table 1, the $ED_{50}$ value of the compound of this invention was 0.30 µg/kg or less, thus indicating that it exerts a very potent inhibitory effect on Bezold-Jarisch reflex. The compounds showed a more prolonged and much more potent action than the control drug. It was, therefore, considered that the compound of this invention has a potent 5-$HT_3$ antagonistic action.

2. Inhibition of cisplatin-induced vomiting

The experiment was performed with reference to the method of Cohen et al. (Cohen, M. L., Bloomquist, W., Gidda, J. S. and Lacefie, W: Comparison of the 5-HT$_3$ receptor antagonist properties of ICS-205-930, GR38032F and Zacopride; J. Pharmacol. Exp. Ther. 248, 197–201 (1989)). In this experiment, beagle dogs of either sex, weighing 8–15 kg, were used. Cisplatin, 2 mg/kg, was administered intravenously and the animals were observed for nausea and vomiting over the subsequent 6 hours. The test compounds were administered intravenously 5 minutes before the administration of cisplatin. The results are shown in Table 2.

TABLE 2

Inhibition of cisplastin-induced vomiting

| Test compound (Example No.) | Dose (mg/kg) | a/b | Vomiting frequency (times) | Latency to vomiting (min) |
|---|---|---|---|---|
| Control group | | 20/20 | 12.2 ± 0.8 | 118.9 ± 5.6 |
| 2 | 0.03 | 2/2 | 6.5 | 192.0 |
| 3 | 0.03 | 2/2 | 1.0 | 215.0 |
| 7 | 0.03 | 4/4 | 2.3 ± 0.6** | 206.8 ± 15.7 |
| 11 | 0.01 | 4/4 | 6.8 ± 1.9* | 149.5 ± 5.4 |
| 12 | 0.001 | 4/4 | 7.0 ± 1.7* | 140.5 ± 13.6 |
| | 0.01 | 4/4 | 3.8 ± 0.5** | 173.8 ± 25.3 |
| ICS-205-930 | 0.03 | 4/4 | 9.5 ± 1.3 | 139.8 ± 13.2 |

*$p < 0.05$, **$p < 0.01$ (Dunnett's method)
a/b = Number of animals which vomited/number of animals used As seen from Table 2, the compound of this invention, at doses of 0.001–0.03 mg/kg, decreased the frequency of cisplatin-induced vomiting and prolonged the latency time to vomiting.

3. Ameliorative effect on scopolamine-induced deficits of learning and memory

The experiment was performed in groups of 10 rats. In the intraperitoneal administration study, the test compound was dissolved in physiological saline and administered, and 15 minutes later 0.3 mg/kg of scopolamine was administered intraperitoneally. In the oral administration study, the test compound was suspended in 0.5% methylcellulose (MC) solution and administered and 30 minutes later 0.3 mg/kg of scopolamine was administered intraperitoneally. Thirty minutes after scopolamine administration, training sessions for a step through-type passive avoidance learning task was carried out and 24 hours after this training, trial sessions were started.

The latency to step-through in the trial sessions was determined up to a maximum of 300 seconds and the result was regarded as a learning result. For the test of significant differences from the control group, the Kruscall-Wallis test and the Fisher test were used. The control group received a physiological saline or MC solution. The results are presented in Tables 3 and 4.

TABLE 3

Ameliorative effect on deficits of learning and memory (rats, intraperitoneal)

| Test compound | Dose (µg/kg) | Latency (sec) |
|---|---|---|
| Control | — | 103.8 ± 43.1 |
| Example 12 | 0.1 | 170.5 ± 43.3 |
| | 0.3 | 183.0 ± 39.6 |
| | 1 | 270.7 ± 29.3** |
| | 3 | 256.3 ± 30.4** |
| | 10 | 163.8 ± 45.6 |
| | 30 | 127.8 ± 46.9 |

**$p < 0.01$

TABLE 4

Ameliorative effect on deficits of learning and memory (rats, oral)

| Test compound | Dose (µg/kg) | Latency (sec) |
|---|---|---|
| Control | — | 110.1 ± 41.6 |
| Example 11 | 0.03 | 214.1 ± 43.8 |
| | 0.1 | 246.5 ± 35.7* |
| | 0.3 | 246.7 ± 35.6* |
| | 1 | 162.0 ± 46.1** |
| Control | — | 111.9 ± 41.4 |
| Example 12 | 0.03 | 108.5 ± 42.0 |
| | 0.1 | 246.3 ± 35.8* |
| | 0.3 | 247.3 ± 35.2* |
| | 1 | 105.5 ± 42.6 |
| | 3 | 139.2 ± 44.0 |

**$p < 0.05$

As shown in Tables 3 and 4, the compound of this invention improved scopolamine-induced deficits of learning and memory.

4. Effect on muscarine M$_1$ receptors

The muscarine M$_1$ receptor binding assay was carried out according to the method of Watson and Yamamura [Life Sci. 32; 3001–3011 (1983)]. Thus, receptor membrane prepared from the rat brain were incubated with 1 nM [$^3$H]pirenzepine in 10 mM Na/K phosphate buffer (pH 7.4) at 25° C. for 60 minutes. As a displacer, 1µM atropine was used. The binding affinity for muscarine M$_1$ receptors was expressed as the concentration of the drug which was required to displace 50 % of the [$^3$H]pirenzepine binding (IC$_{50}$) as shown in Table 5.

TABLE 5

| Effect on muscarine M$_1$ receptors | |
|---|---|
| Test compound | IC$_{50}$ (M) |
| Example 11 | 4.6 × 10$^{-6}$ |
| Example 12 | 1.2 × 10$^{-6}$ |
| Carbachol | 1.2 × 10$^{-5}$ |

As shown in Table 5, the compound of this invention inhibited [$^3$H]pirenzepine binding. The effect was 2 to 10-fold as potent as that of carbachol.

5. Effect on postural reflex (orthostatic hypotension model)

Under anesthesia with urethane and α-chloralose, the rat was immobilized in supine position and a polyethylene cannula was inserted into each of the femoral artery and vein. Blood pressure was measured through the cannula inserted into the artery through a pressure transducer fixed at the level of the rat heart. Each animal was subjected to rapid tilting from the horizontal position through an angle of 60° with the head up and one minute later a return motion to the horizontal position at 5-minute intervals. Tilting was repeated three times and after confirming that a transient hypotensive response was obtained steadily, the drug was administered intravenously.

The compound of this invention in the dose range of 0.01–1 mg/kg inhibited tilting-induced hypotension.

6. Acute toxicity

Six-week-old male mice were used. The test compound was administered intraperitoneally and the animals were observed for mortality over a period of 48 hours. The results obtained with some representative compounds are shown in Table 6.

TABLE 6

| Test compound | Acute toxicity (mice) Dose (mg/kg) | |
|---|---|---|
| (Example No.) | 30 | 50 |
| 2 | 0/4 | 0/4 |
| 3 | 0/4 | 0/4 |
| 4 | 0/4 | 0/4 |
| 6 | | 0/4 |
| 7 | | 0/4 |
| ICS-205-930 | 0/4 | 0/4 |

(Number of dead animals/number of animals used)

It is apparent from Table 6 that none of the test compounds at 50 mg/kg caused death. The safety of the compound of this invention is, thus, evidently clear.

EFFECT OF THE INVENTION

The compound of the invention was found to exhibit a sustained and exceptionally potent serotonin antagonist action, producing excellent antiemetic effects. Moreover, it is very low in toxicity. Therefore, the compound has a broad margin of safety.

Having very beneficial actions not found in the known drugs and a broad margin of safety, the compound can be used for inhibiting the nausea and vomiting associated with anticancer drugs. In addition, based on its serotonin antagonist activity, the compound can be used safely as a digestive tract motor activity regulator, antipsychotic or antianxiety agent.

Furthermore, the compound of the invention can be safely used as a remedy for dementia and a therapeutic and prophylactic drug for orthostatic hypotension and syncope.

We claim:
1. A compound of the formula [I]

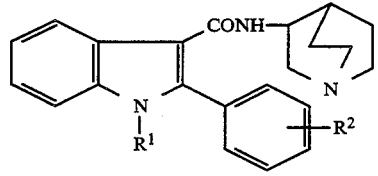

or a pharmaceutically acceptable salt thereof wherein
$R^1$ is lower alkyl and
$R^2$ is hydrogen, halogen, lower alkyl or lower alkoxy.

2. The compound according to claim 1 wherein $R^1$ is methyl.

3. The compound according to claim 1 wherein $R^2$ is halogen.

4. The compound according to claim 1 wherein $R^2$ is $C_{1-4}$ alkoxy.

5. The compound according to claim 1 wherein $R^1$ is methyl and $R^2$ is halogen or $C_{1-4}$ alkoxy.

6. The compound according to claim 1 which is N-(1-azabicyclo[2,2,2]octo-3-yl)-2-(2-methoxyphenyl)-1-methylindole-3-carboxamide and the S isomer thereof.

7. The compound according to claim 1 which is N-(1-azabicyclo[2,2,2]octo-3-yl)-2-(2-chlorophenyl)-1-methylindole-3-carboxamide and the S isomer thereof.

8. A method for treating emesis, nausea, gastrointestinal motor activity, psychosis, anxiety, dementia, migraine, orthostatic hypotension, or other conditions mediated by serotonin antagonist activity in animals and humans which comprises administering to an animal or human in need thereof an effective amount of a serotonin antagonist of the compound according to claim 1.

9. A method for treating emesis, nausea, gastrointestinal motor activity, psychosis, anxiety, dementia, migraine, orthostatic hypotension, or other conditions mediated by serotonin antagonist activity in animals and humans which comprises administering to an animal or human in need thereof an effective amount of a serotonin antagonist of the compound according to claim 2.

10. A method for treating emesis, nausea, gastrointestinal motor activity, psychosis, anxiety, dementia, migraine, orthostatic hypotension, or other conditions mediated by serotonin antagonist activity in animals and humans which comprises administering to an animal or human in need thereof an effective amount of a serotonin antagonist of the compound according to claim 3.

11. A method for treating emesis, nausea, gastrointestinal motor activity, psychosis, anxiety, dementia, migraine, orthostatic hypotension, or other conditions mediated by serotonin antagonist activity in animals and humans which comprises administering to an animal or human in need thereof an effective amount of a serotonin antagonist of the compound according to claim 4.

12. A method for treating emesis, nausea, gastrointestinal motor activity, psychosis, anxiety, dementia, migraine, orthostatic hypotension, or other conditions mediated by serotonin antagonist activity in animals and humans which comprises administering to an animal or human in need thereof an effective amount of a serotonin antagonist of the compound according to claim 5.

13. A method for treating emesis, nausea, gastrointestinal motor activity, psychosis, anxiety, dementia, migraine, orthostatic hypotension, or other conditions mediated by serotonin antagonist activity in animals and humans which comprises administering to an animal or human in need thereof an effective amount of a serotonin antagonist of the compound according to claim 6.

14. A method for treating emesis, nausea, gastrointestinal motor activity, psychosis, anxiety, dementia, migraine, orthostatic hypotension, or other conditions mediated by serotonin antagonist activity in animals and humans which comprises administering to an animal or human in need thereof an effective amount of a serotonin antagonist of the compound according to claim 7.

15. A method for treating emesis, nausea, dementia and psychosis in animals and humans which comprises administering to an animal or human in need thereof an effective amount of a serotonin antagonist of the compound according to claim 1.

16. A method for treating emesis, nausea, dementia and psychosis in animals and humans which comprises administering to an animal or human in need thereof an effective amount of a serotonin antagonist of the compound according to claim 2.

17. A method for treating emesis, nausea, dementia and psychosis in animals and humans which comprises administering to an animal or human in need thereof an effective amount of a serotonin antagonist of the compound according to claim 3.

18. A method for treating emesis, nausea, dementia and psychosis in animals and humans which comprises administering to an animal or human in need thereof an effective amount of a serotonin antagonist of the compound according to claim 4.

19. A method for treating emesis, nausea, dementia and psychosis in animals and humans which comprises administering to an animal or human in need thereof an effective amount of a serotonin antagonist of the compound according to claim 5.

20. A method for treating emesis, nausea, dementia and psychosis in animals and humans which comprises administering to an animal or human in need thereof an effective amount of a serotonin antagonist of the compound according to claim 6.

21. A method for treating emesis, nausea, dementia and psychosis in animals and humans which comprises administering to an animal or human in need thereof an effective amount of a serotonin antagonist of the compound according to claim 7.

22. A pharmaceutical composition for treating emesis, nausea, gastrointestinal motor activity, psychosis, anxiety, dementia, migraine, orthostatic hypotension, or other conditions mediated by serotonin antagonist activity in animals and humans which comprises an effective amount of a serotonin antagonist of the compound according to claim 1 in combination with a pharmaceutically acceptable inert diluent or carrier.

23. A pharmaceutical composition for treating emesis, nausea, gastrointestinal motor activity, psychosis, anxiety, dementia, migraine, orthostatic hypotension, or other conditions mediated by serotonin antagonist activity in animals and humans which comprises an effective amount of a serotonin antagonist of the compound according to claim 2 in combination with a pharmaceutically acceptable inert diluent or carrier.

24. A pharmaceutical composition for treating emesis, nausea, gastrointestinal motor activity, psychosis, anxiety, dementia, migraine, orthostatic hypotension, or other conditions mediated by serotonin antagonist activity in animals and humans which comprises an effective amount of a serotonin antagonist of the compound according to claim 3 in combination with a pharmaceutically acceptable inert diluent or carrier.

25. A pharmaceutical composition for treating emesis, nausea, gastrointestinal motor activity, psychosis, anxiety, dementia, migraine, orthostatic hypotension, or other conditions mediated by serotonin antagonist activity in animals and humans which comprises an effective amount of a serotonin antagonist of the compound according to claim 4 in combination with a pharmaceutically acceptable inert diluent or carrier.

26. A pharmaceutical composition for treating emesis, nausea, gastrointestinal motor activity, psychosis, anxiety, dementia, migraine, orthostatic hypotension, or other conditions mediated by serotonin antagonist activity in animals and humans which comprises an effective amount of a serotonin antagonist of the compound according to claim 5 in combination with a pharmaceutically acceptable inert diluent or carrier.

27. A pharmaceutical composition for treating emesis, nausea, gastrointestinal motor activity, psychosis, anxiety, dementia, migraine, orthostatic hypotension, or other conditions mediated by serotonin antagonist activity in animals and humans which comprises an effective amount of a serotonin antagonist of the compound according to claim 6 in combination with a pharmaceutically acceptable inert diluent or carrier.

28. A pharmaceutical composition for treating emesis, nausea, gastrointestinal motor activity, psychosis, anxiety, dementia, migraine, orthostatic hypotension, or other conditions mediated by serotonin antagonist activity in animals and humans which comprises an effective amount of a serotonin antagonist of the compound according to claim 7 in combination with a pharmaceutically acceptable inert diluent or carrier.

29. A pharmaceutical composition for treating emesis, nausea, dementia and psychosis in animals and humans which comprises an effective amount of a serotonin antagonist of the compound according to claim 1 in combination with a pharmaceutically acceptable inert diluent or carrier.

30. A pharmaceutical composition for treating emesis, nausea, dementia and psychosis in animals and humans which comprises an effective amount of a serotonin antagonist of the compound according to claim 2 in combination with a pharmaceutically acceptable inert diluent or carrier.

31. A pharmaceutical composition for treating emesis, nausea, dementia and psychosis in animals and humans which comprises an effective amount of a serotonin antagonist of the compound according to claim 3 in combination with a pharmaceutically acceptable inert diluent or carrier.

32. A pharmaceutical composition for treating emesis, nausea, dementia and psychosis in animals and humans which comprises an effective amount of a serotonin antagonist of the compound according to claim 4 in combination with a pharmaceutically acceptable inert diluent or carrier.

33. A pharmaceutical composition for treating emesis, nausea, dementia and psychosis in animals and humans which comprises an effective amount of a serotonin antagonist of the compound according to claim 5 in combination with a pharmaceutically acceptable inert diluent or carrier.

34. A pharmaceutical composition for treating emesis, nausea, dementia and psychosis in animals and humans which comprises an effective amount of a serotonin antagonist of the compound according to claim 6 in combination with a pharmaceutically acceptable inert diluent or carrier.

35. A pharmaceutical composition for treating emesis, nausea, dementia and psychosis in animals and humans which comprises an effective amount of a serotonin antagonist of the compound according to claim 7 in combination with a pharmaceutically acceptable inert diluent or carrier.

\* \* \* \* \*